(12) United States Patent
Contreras Ramos et al.

(10) Patent No.: US 10,807,919 B2
(45) Date of Patent: Oct. 20, 2020

(54) BIOFERTILIZER TO INCREASE AGRICULTURAL YIELD

(71) Applicants: CENTRO DE INVESTIGACION Y ASISTENCIA EN TECNOLOGIA Y DISENO DEL ESTADO DE JALISCO A-C-, Guadalajara (MX); ORGANIK BOLLUK S.P.R. DE R.L. DE C.V., Guadalajara (MX)

(72) Inventors: Silvia Maribel Contreras Ramos, Guadalaljara (MX); Gustavo Davila Vazquez, Guadalajara (MX); Flor Flores Hernandez, Guadalajara (MX); Erika Nahomy Marino Marmolejo, Guadalajara (MX); Roberto Emmanuel Bolanos Rosales, Guadalajara (MX)

(73) Assignees: Centro De Investigacion Y Asistencia En Tecnologia Y Diseno Del Estado De Jalisco A.C., Jalisco (MX); Organik S.P.R. De R.L. DE C.V., Jalisco (MX)

( * ) Notice: Subject to any disclaimer, the term of this patent is extended or adjusted under 35 U.S.C. 154(b) by 0 days.

(21) Appl. No.: 15/570,425

(22) PCT Filed: Nov. 17, 2016

(86) PCT No.: PCT/MX2016/000118
§ 371 (c)(1),
(2) Date: Oct. 30, 2017

(87) PCT Pub. No.: WO2017/086770
PCT Pub. Date: May 26, 2017

(65) Prior Publication Data
US 2019/0077720 A1    Mar. 14, 2019

(30) Foreign Application Priority Data
Nov. 19, 2015   (MX) .................. MX/a/2015/015919

(51) Int. Cl.
| C05F 11/08 | (2006.01) |
| A01N 63/30 | (2020.01) |
| C05F 17/00 | (2020.01) |
| A01N 59/06 | (2006.01) |
| C12R 1/38 | (2006.01) |
| C12R 1/22 | (2006.01) |
| C12R 1/39 | (2006.01) |
| A01N 63/27 | (2020.01) |
| C12N 1/20 | (2006.01) |
| A01N 63/20 | (2020.01) |

(52) U.S. Cl.
CPC .............. C05F 11/08 (2013.01); A01N 59/06 (2013.01); A01N 63/20 (2020.01); A01N 63/27 (2020.01); A01N 63/30 (2020.01); C05F 17/00 (2013.01); C12N 1/20 (2013.01); C12R 1/22 (2013.01); C12R 1/38 (2013.01); C12R 1/39 (2013.01)

(58) Field of Classification Search
CPC .......... C05F 11/08; C05F 17/00; A01N 63/04; A01N 63/30; A01N 63/27; A01N 59/06; C12N 1/20; C12R 1/39; C12R 1/22; C12R 1/38
See application file for complete search history.

(56) References Cited

U.S. PATENT DOCUMENTS

| 3,018,225 A * | 1/1962 | Long .................. C12P 19/42 435/86 |
| 4,952,229 A | 8/1990 | Muir |
| 2008/0190158 A1 | 8/2008 | Amy |
| 2013/0202562 A1 | 8/2013 | Wood |
| 2014/0120601 A1* | 5/2014 | Bywater-Ekegard .... C12N 1/12 435/252.5 |
| 2015/0218568 A1* | 8/2015 | Jones .................. A01N 37/46 504/117 |

FOREIGN PATENT DOCUMENTS

| WO | WO2007116245 | 10/2007 | |
| WO | WO2010109436 | 9/2010 | |
| WO | WO-2014201044 A2 * | 12/2014 | ............. A01N 63/00 |

OTHER PUBLICATIONS

Gamble, T.N., Numerically Dominant Denitrifying Bacteria from World Soils, Apr. 1977, Applied and Enviromental Microbiology, vol. 33, No. 4, pp. 926-939. (Year: 1977).*

Ivanova, E.P. Abstract, Pubmed Abstract. [online]. Int. J. Syst Evol Microbiology, 2009 [retrieved on Feb. 2, 2019]. Retrieved from the Internet:<URL:https://www.ncbi.nlm.nih.gov/pubmed/19622656>. 2 pages. (Year: 2009).*

(Continued)

*Primary Examiner* — John Pak
*Assistant Examiner* — Andriae M Holt
(74) *Attorney, Agent, or Firm* — Defillo & Associates, Inc.; Evelyn A. Defillo

(57) ABSTRACT

This invention consists of a consortium of plant-growth promoting microorganisms including *Pseudomonas stutzeri*, *Pseudomonas denitrificans*, *Pseudomonas resinovorans*, *Pseudomonas brassicacearum*, *Pseudomonas fluorescens*, *Shimwellia blattae* and *Klebsiella oxytoca*. The bacterial consortium along with a vehicle suitable for agricultural application, form a biofertilizer useful to enhance agricultural yield when applied to cultivation plants. The biofertilizer described present a long shelf life and preserve a high cell density along the time.

14 Claims, 6 Drawing Sheets
Specification includes a Sequence Listing.

(56) References Cited

OTHER PUBLICATIONS

Stewart Publication, [online]. Univ of CA , Davis, 2004 [retrieved on Feb. 19, 2019]. Retrieve from the Internet:<URL:https://portal.nifa.usda.gov/web/crisprojectpages/0183560- nitrogen-regulation-of-nitrate-assimilation-by-the-soil-bacterium-klebsiella-oxytoca.html> 5 pages (Year: 2004).*
Egamberdiyeva, D., Characterization of Pseudomonas Species Isolated from the Rhizosphere of Plants Grown in Serozem Soil, Semi-Arid Region of Uzbekistan, 2005, The Scientific World Journal, vol. 5, pp. 501-509. (Year: 2005).*
Kang Abstract, Klebsiella Oxytoca C1036 and Plant Growth Promotion, Disease Control and Environmental Stress Reduction Methods Using the Same, 2008, Abstract for KR100800566B1, 2 pages. (Year: 2008).*
Zaidi Alams et al.: Role of plant growth promoting rhizobacteria in sustainable production of vegetables: Current perspective, Scientia Horticulture, Elsevier,Amsterdam, NL, Jul. 28, 2015, vol. 193, pp. 231-239, ISSN 0304-4238, DOI:doi:10.1016/j.scienta.2015.07.020 the whole document.

* cited by examiner

BIOFERTILIZER TO INCREASE AGRICULTURAL YIELD

CROSS REFERENCE TO RELATED APPLICATION

This application is a national stage entry of PCT/MX2016/050044 filed Nov. 17, 2016, under the International Convention claiming priority over Mexican Patent Application No. MX/a/2015/015919 filed Nov. 19, 2015.

FIELD OF INVENTION

This invention is related to agricultural biotechnology, and more concretely with a biofertilizer involving a consortium of plant growth promoting bacteria, which increases agricultural output.

BACKGROUND OF THE INVENTION

Sustainable agricultural production requires strategies aimed to decrease inputs such as water, fertilizer or pesticides to ensure plant biomass yield at low cost without affecting soil fertility.

Biofertilizers are one of the alternatives to succeed on it. They are also called bacterial inoculum, microbial inoculant, bacterial fertilizer, bioinoculant, bacterial or bacteria consortia, among other names. They consist of an association of microbial populations whose function is to render nutrients available to plants so they can increase productivity or yield without compromising soil health. Those microbial consortia are not restricted to just bacteria, they can contain also fungi or other microorganisms.

Since the register or U.S. Pat. No. 578,013 patent of *Rhizobium* spp, almost 120 years ago, the use of microorganisms for agricultural purposes has increased. The most used bacterial group for agricultural purposes are rhizobacteria, commonly denominated plant growth promoting rhizobacteria (PGPR). They colonize plant roots and have several functions like: nitrogen fixation, phosphorus solubilization, phytohormone production (auxins and cytokinines), production of root-growth promoting volatile compounds (e.g., 2-3-butanediol), nitrogen oxidation from organic sources, siderophores production, among others (Bruto M, Prigent-Combaret C, Muller D, Moënne-Loccoz Y. (2014) Analysis of genes contributing to plant-beneficial functions in plant growth-promoting rhizobacteria and related Proteobacteria. Scientific Reports. 4:6261). Some of these bacteria also show features that allow them to control pathogens, since they produce antibiotics or compounds that are toxic to specific pathogens (Haas D. Y Défago G. (2005) Biological control of soil-borne pathogens by fluorescent pseudomonads. Nature Reviews Microbiology 3, 307-319). The most commonly used rhizobacteria for agriculture are *Azotobacter* spp., *Bacillus megaterium* to solubilize phosphorus, *Flavobacterium* sp., *Acetobacter* sp., *Azospirillum* sp. (Bashan Y. (1998) Inoculants of plant growth-promoting bacteria for use in agriculture. Biotechnology Advances, 16, (4): 729-770; Bashan Y. & L. E. de-Bashan & S. R. Prabhu & Juan-Pablo Hernandez. (2014) Advances in plant growth-promoting bacterial inoculant technology: formulations and practical perspectives (1998-2013). Plant Soil, 378:1-33; Haas D. and Défago G. (2005) Biological control of soil-borne pathogens by fluorescent pseudomonads. Nature Reviews Microbiology 3, 307-319); In the case of fungi, the most commonly used is *Trichoderma* sp. (Haas D. and Défago G. (2005) Biological control of soil-borne pathogens by fluorescent pseudomonads. Nature Reviews Microbiology 3, 307-319).

Several biofertilizers using PGPR bacterial consortia have been developed. For instance, Chinese patent application number CN101468924A describes a bio-organic fertilizer involving a mixture of *Pseudomonas stutzeri* and *Bacillus megaterium* in a fermentation liquid.

German patent application number DE102005031397A1 implies a formulation of a granulated fertilizer with a mixture of metals, enzymes and organisms components such as bacteria *Bacillus subtilis*, *Nitrosomonas* and *Klebsiella pneumoniae*, and algae *Chondrus crispus* and *Gigartina mamillosa*.

In some cases, the biofertilizer formulation contains a large amount of microorganism species, as the one described in the american patent U.S. Pat. No. 4,952,229 including: *Bacillus thuringiensis, Bacillus subtillis, Arthrobacter globiformis, Arthrobacter agilis, Nocardia coarallina, Pseudomonas fluorescens, Bacteroides succinogenes, Bacteroides lipolyticum, Kurthis zopfil, Brevibacterium lipolyticum, Aspergillus terreus, Rhizopus arrhizus, Azotobacter chroococcum, Azotobacter paspali, Myrothecium verrucaria, Trichoderma viride, Phanerochaete chrysosporium, Pseudomonas halestorga, Pseudomonas calcis, Pseudomonas gelatic, Pseudomonas marinoglutionosa, Pseudomonas nigriaciens, Brevibacterium stationis, Arthrobacter citreus, Arthrobacter luteus, Arthrobacter simplex, Azosprillum brasilienese, Azosprillum lipoferum, Bacillus brenis, Bacillus macerans, Bacillus pumilus, Bacillus polymyxa, Pseudomonas putida, Streptomycus cellulasae, Streptomycus fradiae, Streptomucus griseoflavus*, and *Acinetobacter lwoffii*; which can be applied directly in leaves or soil.

As other example, in the Mexican patent MX328184B a biofertilizer is made from the bacterial strains: *Pseudomonas fluorescens, Herbaspirillum frisingense, Herbaspirillum* sp. and *Bacilus subtilis*.

Rhizobacteria can be used in consortium, but also as a single strain component, as it has been described in patents CN103010841A, CN101709217B, CN102827792B, U.S. Pat. Nos. 4,952,229 y 5,503,651. Also, the international publication WO2013/076687A2, includes one strain of *Pseudomonas fluorescens* able to fix nitrogen. Chinese patent CN103525830B has a mutant of the wild type strain *Pseudomonas stutzeri*.

As described above, the state-of-art techniques include diverse bacterial consortia or one strain, which have been developed to enhance or increase crop yield. Nevertheless, such microorganism consortia or strains show a steeply decrease when applied to soil, most biofertilizers have low cell density, like $1\times10^4$ up to $1\times10^6$ CFU/mL (CFU=colony forming units), and only a few report to have $1\times10^9$ CFU/mL. Hence, agricultural output renders low yields in spite of adding such biofertilizers.

Furthermore, most of the commercially available biofertilizers are sold on a solid or powder basis. These dosage forms have low humidity that leads to a decrease in cell viability and in cell density. This effect is more intense, the longer the storage period, which is why the storage or shelf life is less than eight months. Because of that and in order to keep those problems of biofertilizers at minimum, a new biofertilizer formulation with high cell density and a large storage lifetime has been developed and described in the present invention.

OBJECTIVE OF THE INVENTION

Regarding the flaws of the state-of-art techniques, the present invention aims to provide a plant growth promoting bacterial (PGPR) consortium, which is adequate to be used as a biofertilizer.

Also, the present invention aims to provide a biofertilizer to increase crop yield with a longer storage life while preserving a high cell density.

Furthermore, the present invention aims to provide a biofertilizer useful to enhance agricultural output with a superior yield.

SUMMARY OF THE INVENTION

The present invention refers to a consortium of plant growth promoting bacteria consisting of *Pseudomonas stutzeri; Pseudomonas denitrificans, Pseudomonas resinovorans, Pseudomonas brassicacearum, Pseudomonas fluorescens, Shimwellia blattae* and *Klebsiella oxytoca*.

Another aspect of the present invention refers to the biofertilizer enhancing agricultural yield, which comprises the consortium of plant growth promoting bacteria and a vehicle suitable for agricultural application.

An additional aspect of the present invention refers to the application of the biofertilizers enhancing agricultural yield, which comprises the consortium of plant-growth promoting bacteria and a vehicle suitable for agricultural application.

BRIEF DESCRIPTION OF DRAWINGS

The innovative aspects, which are considered characteristic of present invention are to be established in the dependent claims. However, some modalities, specifications, aims and advantages of the invention will be better understood along with the description and reading of the figures or drawings, in which:

DETAILED DESCRIPTION OF THE INVENTION

Figure 1:
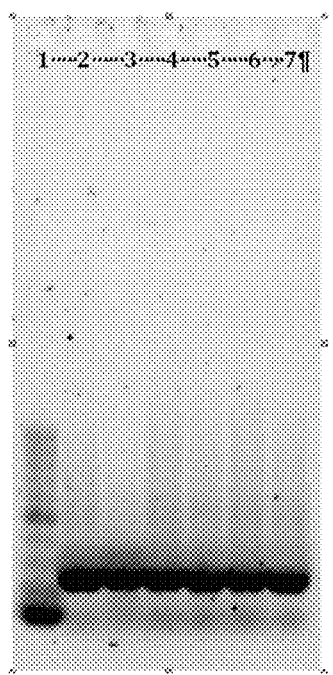
FIG. 1 shows the electrophoresis gel image of PCR product. Lane 1 corresponds to 100 bp (DNA ladder) marker, lanes 2 to 7 corresponds to PCR product of V3 16S region of M9, M19, M25, M28 mixtures.

The present invention is related to a consortium of plant-growth promoting bacteria (PGPR) comprising *Pseudomonas stutzeri, Pseudomonas denitrificans, Pseudomonas resinovorans, Pseudomonas brassicacearum, Pseudomonas fluorescens, Shimwellia blattae* and *Klebsiella oxytoca*; This bacterial consortium was deposited in ATCC (American Type Culture Collection) as a International Authority for Repository of Budapest Treaty for the International Recognition of Microorganism Repositary for Patent applications, with the number PTA-122530.

As for the present invention, henceforth, bacterial consortium will refer to the ensemble of microbial population used for agricultural purposes.

In the preferred mode for present invention, bacterial consortium is formed one or more of four mixtures containing bacteria, which in their turn, are comprised in the consortium. These mixtures are: the first one comprises *Pseudomonas stutzeri, Pseudomonas denitrificans* and *Pseudomonas resinovorans*, the second consists of *Pseudomonas brassicacearum* and *Pseudomonas Fluorescens*; the third mixture consists of *Pseudomonas brassicearum* and *Shimwellia blattae*; and the fourth mixture consists of *Klebsiella oxytoca* and *Shimwellia blattae*.

Single bacteria strain or their mixtures, both of which are described here, could be isolated and cultured in any medium containing them. Preferably, bacterial comprised in the consortium could be isolated from a fermentative process on organic substrates. Such a method involves organic substrates selected from one or a mixture of more of the following: earthworm humus, milk whey, molasses or cow manure in an anaerobic environment for two months. Preferably, fermentation process may be carried out at 18-35° C. temperature range. From the latter process, an organic fertilizer, from which the bacterial consortium of the present invention could be isolated by means of any conventional state-of-art culture technique.

As an alternative, bacteria comprising the consortium described in the present invention could be isolated from soils where an organic biofertilizer (described above) was applied, with the addition of other agents chosen from other biofertilizers, fishery wastes, cow manure or a combination of them. Preferably, soils from which bacteria comprising the consortium described in the present invention may be cultivated with organic cucumber and found in a protected greenhouse.

In other aspect of the present invention, a biofertilizer comprising a plant growth promoting bacteria (PGPR) consortium comprising *Pseudomonas stutzeri, Pseudomonas denitrificans, Pseudomonas resinovorans, Pseudomonas brassicacearum, Pseudomonas fluorescens, Shimwellia blattae* and *Klebsiella oxytoca*; and a vehicle suitable for agricultural use.

As for the present invention, the term "biofertilizer" refers to an input formulated with at least one plant-growth promoting bacteria (PGPR), which enhances agricultural yield when applied in cultivation.

In the alternative mode of the present invention, the bacterial consortium is formed by a mixture of bacteria, or combined with any other plant-growth promoting bacteria or beneficial organisms such as fungi, rhizobacteria or algae, either native or mutants, and include any derived or any metabolite obtained from them.

In a preferable mode of the present invention, in which bacteria consortium is formed by one or more mixtures of bacteria, the culture of those mixtures are combined to obtain the biofertilizer in accordance to the principles of the present invention in the following proportions for a liter of a vehicle suitable for agricultural use: 15 to 60 mL of first mixture; 5 to 30 mL of second mixture; 10 to 60 mL of third mixture; and 5 to 30 mL of fourth mixture; cell densities of the mixtures are in the $1 \times 10^9$ a $1 \times 10^{12}$ CFE/mL range, preferably $1 \times 10^{11}$ CFU/mL.

In a preferable mode of present invention, cell density of biofertilizers, as final product is in the $1 \times 10^9$ to $1 \times 10^{17}$ CFU/mL range; but even more preferably, the cell density of biofertilizers is in the $1 \times 10^9$ to $1 \times 10^{13}$ CFU/mL range.

Regarding the vehicle suitable for agriculture, in a preferable mode of the present invention, the vehicle consists of an aqueous solution containing one or more of the following components according to the indicated final concentration: 3 to 15 g/L dehydrated milk whey; 0.1 to 0.4 g/L potassium chloride; 0.2 to 1.0 g/L ammonium sulfate; 0.001 to 0.005 g/L ferrous sulfate; 0.2 to 0.8 g/L magnesium sulfate; and/or 0.002 to 0.009 g/L manganese sulfate.

In a preferable mode of the present invention, the biofertilizer comprises optionally, a cell protectant, which is a substance that confers stability to cell membrane and therefore to the whole cell. With it, the biofertilizer keeps a cell density about $1 \times 10^9$ CFU/mL at least, for 8 months, thus increasing its storage life. Such a cell protectant is selected among sodium alginate, gum arabic, polyvinylpyrrolidone, polyethylenglycol, trehalose, glycerol, high-density carboxymethylcelulose, polysorbate 20 or a mixture of them. In an even more preferable mode of the present invention, the cell protectant is added in a final concentration of 0.1 to 2.5% of the vehicle.

In other aspect of the present invention, the use of the biofertilizers as depicted in the present invention is described to enhance crop yield. The use comprises application of such biofertilizer in cultivation plants.

The biofertilizers of the present invention is useful to increase crop yield in any type of plant and it is not limited to be used in a specific type of soil. Preferably, biofertilizer is intended to be applied next to plant stem at soil level by draining or spraying it, in doses of 1-2 L per hectare, with 200 L of irrigation water by draining or in a dose of 3-5 mL per plant, applied close to their stems, by draining or aspersion, in a single dose at the beginning of the productive cycle of plants.

The present invention will be better understood with the following examples, which are presented only for illustrative purposes to allow full comprehension of the preferable modes of the present invention without reducing the modes, but extending them to any other mode or application based on that described in the present document.

EXAMPLES

Example 1

In this example, isolation and molecular identification of consortium bacteria is described according to the principles of the present invention.

Plant growth promoting bacteria (PGPR) were isolated from a fermentative process of a mixture with the following organic substrate: molasses, earthworm hummus and milk whey. 10-g samples of a mixture of the organic substrates were homogenated in 90 mL of sterile 0.9% saline solution. From this solution, serial dilutions were done up to $10^{-5}$. One mL of each solution was inoculated in different known selective media, like ELMAR (or YEMACR) medium (yeast extract, mannitol, agar and congo red), AGEL (or AGYE) medium (agar, glucose and yeast extract); AG or AC medium (arginine-glycerol agar or caseinate-arginine agar) and in ammonium broth with or without agar. Media were incubated at 28° C. for 72 hours. From a subsequent re-inoculation, which helped to select colonies to be cultured in same medium, mixtures were obtained: M9 (consisting of *Pseudomonas stutzeri*, *Pseudomonas denitrificans* and *Pseudomonas resinovorans*), M19 (consisting of *Pseudomonas brassicacearum* and *Pseudomonas Fluorescens*), M25 (consisting of *Pseudomonas brassicacearum* and *Shimwellia blattae*) and M28 (consisting of *Klebsiella oxytoca* y *Shimwellia blattae*).

To carry out the molecular identification of bacteria of the previously described M9, M19, M25, M28 mixtures, genomic DNA was obtained from liquid cultures by means of ZR-Soil fungal/bacterial DNA miniprep extraction kit (Zymo research). One total DNA band was visualized in 1% agarose gel stained with Gel Red (BIOTUM). Afterwards, a fragment of the hypervariable V3 of bacterial 16S ARNr was amplified by using Q5 polymerase (New England, Biolabs) in PCR.

The primers used in PCR reaction were:

C356F
(5'-CGCCCGCCGCGCCCCGCGCCCGTCCCGCCGCCCCGCCCCCTACG

GGAGGCAGCAG-3')
and 517R
(5'-ATTACCGCGGCTGCTGG-3').
Primer C356F contained a GC-clamp (in bold).

Figure 2:
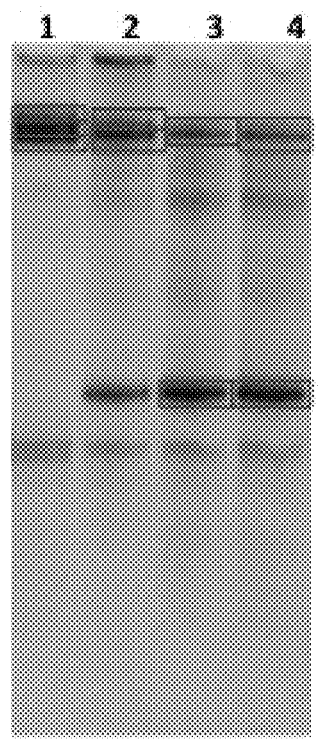
FIG. 2 shows the denaturing-gradient gel electrophoresis (DGGE) image of V3 16S PCR product of M9, M19, M25 y M28 mixtures. Lane 1 corresponds to M9 mixture, lane 2 to M19, lane 3 to M25, and lane 4 to M28 mixture.

PCR product was visualized in 1% agarose gel stained with Gel Red (FIG. 1). In FIG. 1, bands with 240 bp size from each PCR product were observed. Amplified products from PCR were analyzed by denaturing-gradient gel electrophoresis (DGGE) using a 10% polyacrylamide gel in 1× TAE buffer (20 mM Tris, 10 mM sodium acetate, 0.5 mM EDTA, pH 7.4) with a 30 to 60% urea-formamide denaturing gradient. DGGE was performed at 60 °C at 70 V constant voltage during 14 h. After staining with Gel Red for 30 min, gel was observed under UV light (FIG. 2). In FIG. 2, the different bands of each mixture: M9, M19, M25 and M28 are observed in their respective lane. Seven bands corresponding each to a different bacteria conforming the consortium of the present invention, also correspond to the mixtures M9, M18, M25 and M28. Dominant bands, were cut, re-amplified, purified and sent for DNA sequencing in Macrogen, Md., USA. Sequences were analyzed with Bioedit v.7.0.9 software (Ibis Bioscience, Carlsbad, Calif., USA) and submitted to the non-redundant sequences database of GenBank using BLAST program and to Ribosomal Database Project (RDP) database (http://rdp.cme.msu.edu/index.jsp) for bacteria identification. Identification of bacteria is showed in table 1. Homology was found to be 97-100% for the bacteria conforming the present invention.

TABLE 1

| Identification of bands in DGGE | Identity | Homology | Access number |
|---|---|---|---|
| M9-1 | *Pseudomonas stutzeri* | 99% | NR_103934.1 |
| M9-2 | *Pseudomonas denitrificans* | 99% | NR_102805.1 |
| M9-3 | *Pseudomonas resinovorans* | 99% | EU497964 |
| M19-1 | *Pseudomonas brassicacearum* NM421 | 100% | NR_074834.1 |
| M19-2 | *Pseudomona flourescens* | 100% | AM048789.1 |
| M25-1 | *Pseudomonas brassicacearum* NM421 | 88% | NR_074834.1 |
| M25-2 | *Shimwellia blattae* | 98% | NR_074908.1 |
| M28-1 | *Klebsiella oxytoca* | 97% | NR_102982.1 |
| M28-2 | *Shimwellia blattae* | 99% | NR_074908.1 |

Example 2

This example describes the obtainment of bacterial consortium according to the principles of the present invention.

To obtain the bacterial consortium according to the principles of the present invention, mixtures of bacteria isolated from the mixtures of the previous example, M9, M19, M25 and M28 were prepared by taking them with the bacteriological loop and inoculating them in liquid SRS (Sundara, Rao and Sinha) medium, which were then cultured during 12 hours at 28° C. For each mixture, a final optical density of 0.200-0.260 at 600 nm was obtained, which is equivalent to a cell density of $1\times10^{11}$ to $1\times10^{12}$ CFU/mL.

Example 3

In this example, the obtaining the biofertilizer according to the principles of the present invention is described.

To obtain the biofertilizer (BF) In accordance with the principles of the present invention, a culture of the bacterial mixtures obtained in accordance with the previous examples: M9, M19, M25 and M28, were inoculated in the following proportions: 60 mL/L M9, 60 mL/L M19, 30 mL/L M25, and 30 mL/L M28, in a vehicle containing 0.2 g/L potassium chloride, 0.2 g/L sodium chloride, 10 g/L milk whey, 0.5 g/L ammonium sulfate, 0.002 g/L ferrous sulfate, 0.3 g/L magnesium sulfate and 0.004/L manganese sulfate, and incubated 24 hours at 28° C. until a cell density of $1\times10^{13}$ to $4.45\times10^{13}$ CFU/mL is obtained.

Subsequently, sodium alginate was added as a cell protectant in a final concentration of 0.1% w/v to obtain the biofertilizer.

Example 4

Figure 3:
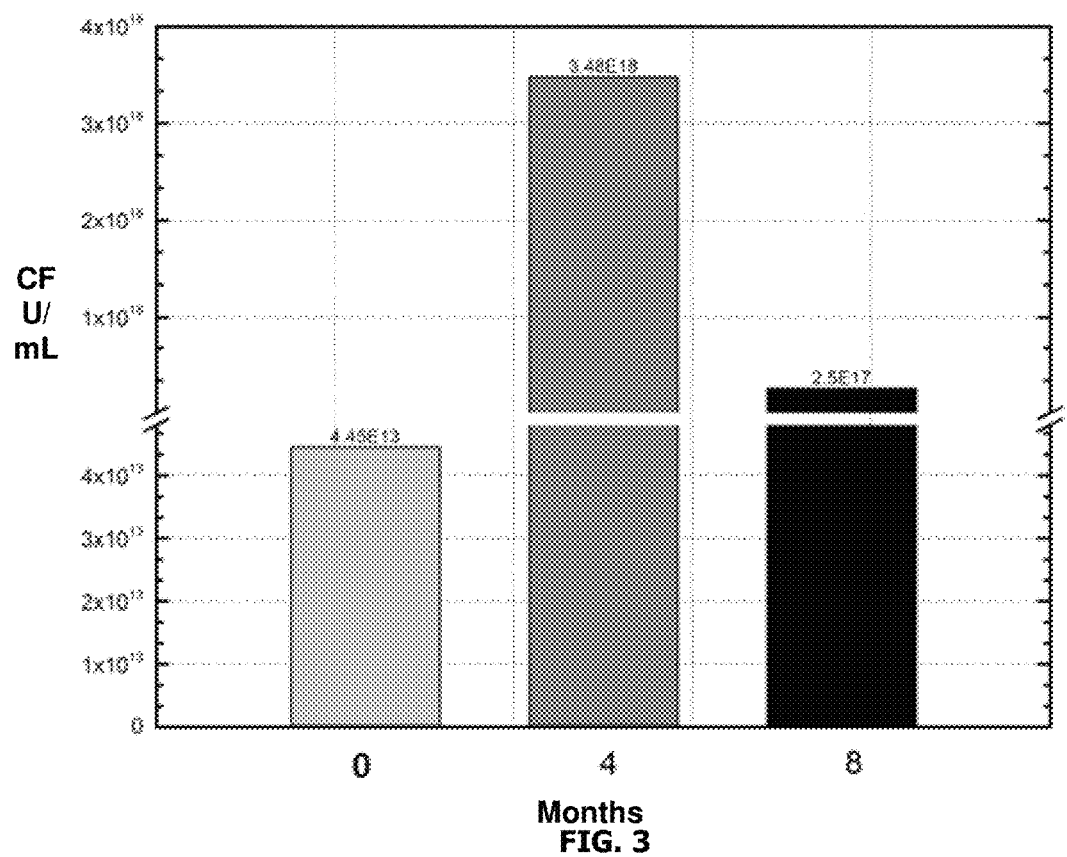
FIG. 3 shows a plot of biofertilizer cell viability through time, when stored at room temperature (25±5° C.)

To assay the viability and longer shelf, the biofertilizer obtained in accordance with the example 3, was stored at room temperature (25° C.±5). Subsequently, viable count was carried out a 0, 4 and 8 months, by using colony count after serial dilutions in a plate with 500 μL of each dilution in a medium made of 5 g/L tryptone, 1 g/L yeast extract, 1 g/L glucose and 18 g/L agar-agar. Results are presented in FIG. 3, where it is easily observed that the biofertilizers of the present invention keeps a viable cell count of $4.45\times10^{13}$ and $2.5\times10^{17}$ CFU/mL during a period of 8 months.

Example 5

Figure 4:
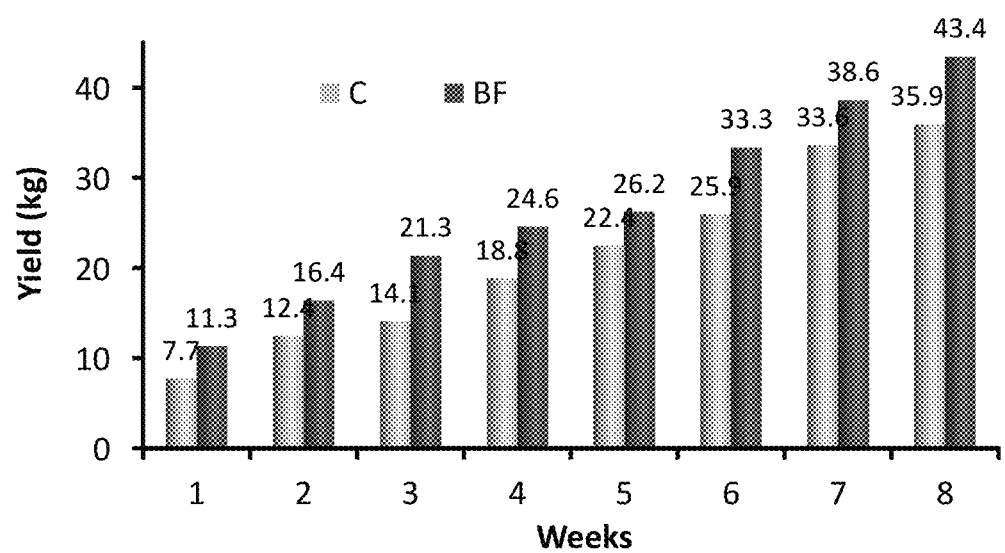
FIG. 4 shows a plot to evaluate the yield of the biofertilizer (from the present invention) on cucumber cultivation. Biofertilizer was applied on 30-days old plants, and yield was evaluated during eight weeks of cultivation cycle.

To assay the yield of the biofertilizers described in example 3, 25 plants from cucumber cultivation were selected and grown in greenhouse conditions, receiving normal nutrition by irrigation. Similar characteristics of height and row conditions were used, also including 30 days of cultivations from transplant and being in productive cycle. To those plants, the biofertilizers was added according to the present invention at a ell density of $1.9\times10^{13}$ CFU/mL, close to plant stems, at soil level and at a single dose of 3 mL/plant. During 8 weeks, plants were monitored and compared to the control (with no biofertilizers added). Results from the accumulated production (AP or PA) average are presented in FIG. 4, where is observed that, after 8 weeks, a 26% increase in average yield was obtained with the biofertilizer application.

Example 6

Figure 5:
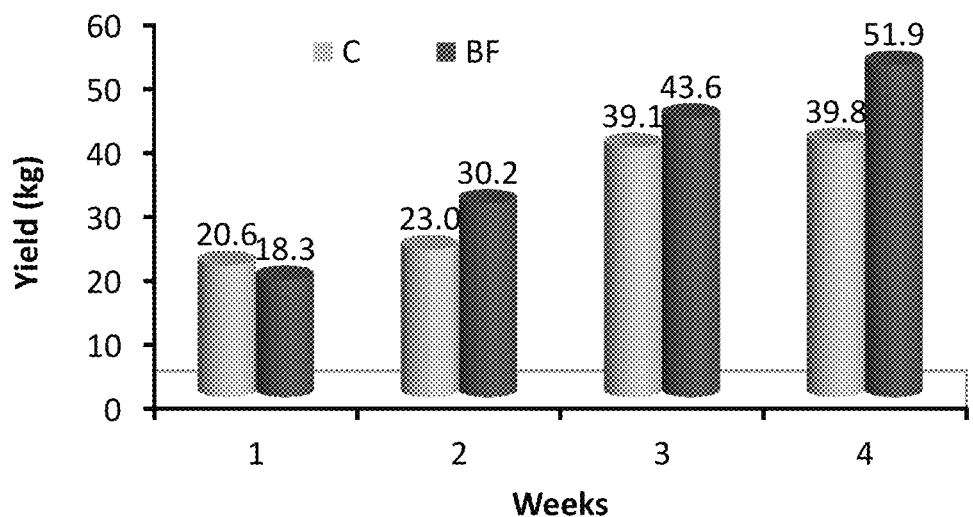
FIG. 5 contains a plot showing the yield of the biofertilizer (of the present invention) after application on 60 days-old cultivation during four weeks of productive cycle.

To assess the yield of the biofertilizer, 25 plants from cucumber plantation in greenhouse conditions were nurtured normally via irrigation system. They were intended to have similar characteristics height and row conditions in greenhouse; also, they had 60 days of culture after transplantation and 30 days of productive cycle. Subsequently, a similar procedure was carried out as in example 5. A 18% yield increase was observed after biofertilizer addition compared to control Results can be observed in FIG. 5.

Example 7

Figure 6:
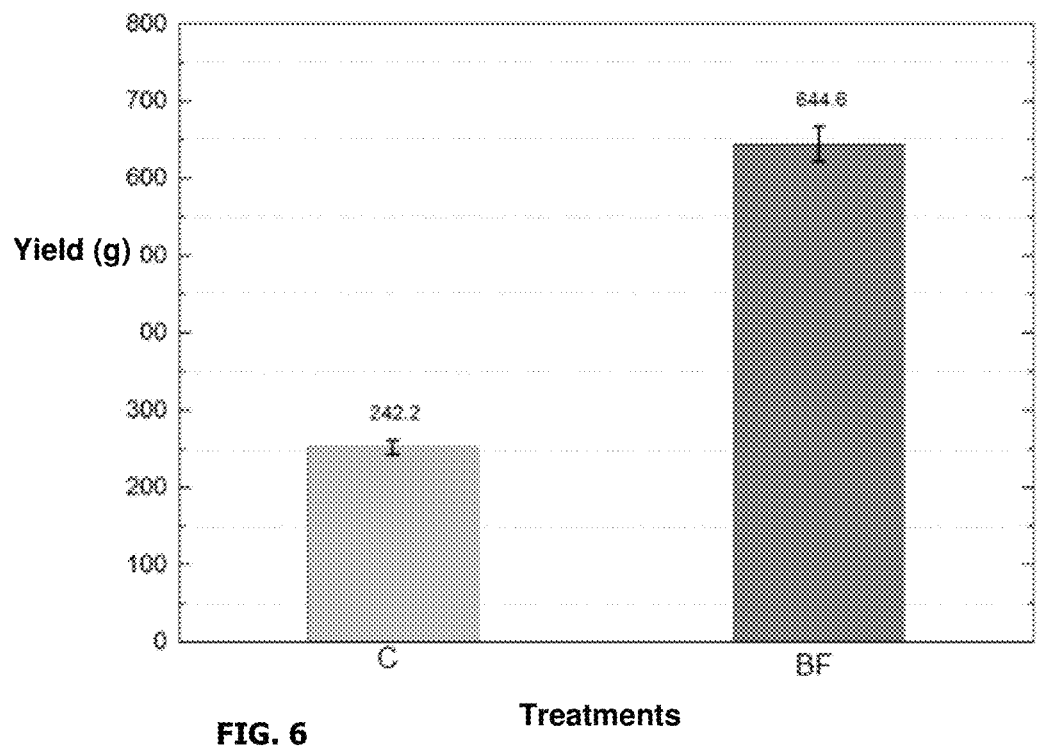
FIG. 6 contains a plot showing the yield of the biofertilizer upon bean (*P. vulgaris*) culture.

To assess yield of the biofertilizer, 10 bean plants were chosen after 15 days of germination and transplanted to a low-till soil in greenhouse conditions. Biofertilizer was added at $2.9\times10^{13}$ CFU/mL in a single dose of 3 mL/plant. Bean pods were collected after 75 days, their dry weight was measured and compared with bean pods from 10 control plants treated equally. Results are presented in FIG. 6, they show an agricultural output of 644.6 g (64 g/plant) when biofertilizer was applied, while control plants gave an agricultural output of 242.2 g (25 g/plant).

Example 8

Figure 7:
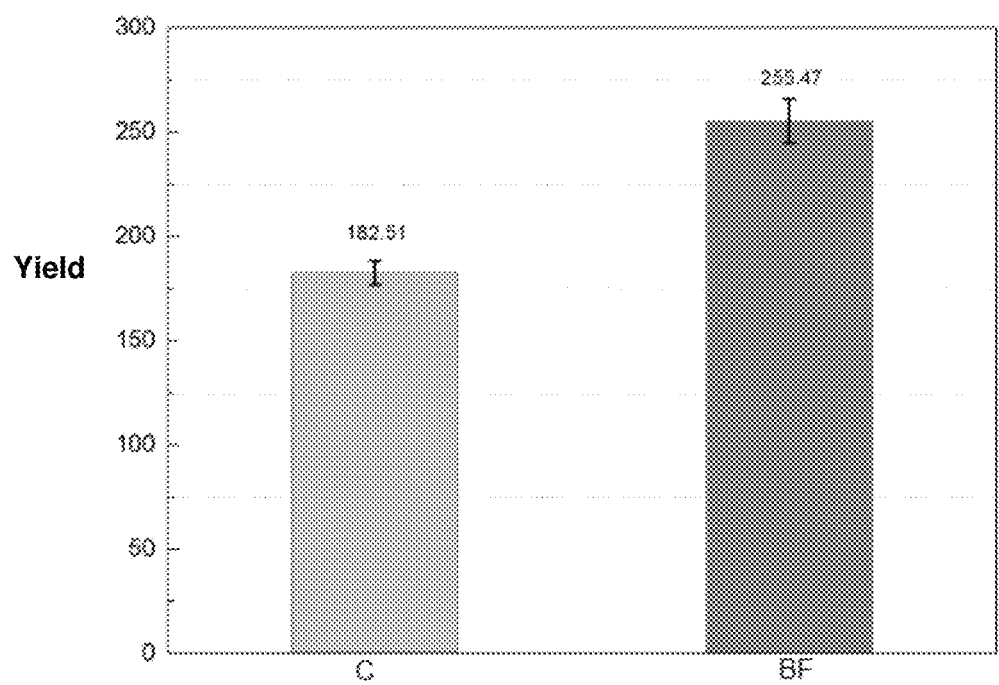
In FIG. 7 plot, yield of the biofertilizer on spring onion (*A. fistulosum*) culture is showed.

To assess the yield of the biofertilizer, 20 spring onion plants were selected after 15 days of germination, and transplanted to a low-till soil in greenhouse conditions. Biofertilizer described in the present invention was applied in a single dose of 3 mL/plant with a cell density of $2.4\times10^{13}$ CFU/mL. After 75 days, plants were harvested and accumulation weight of the onion bulbs were measured and compared to control plants. The latter gave 182.5 g (9.1 g/plant) while plants treated with biofertilizer yielded 255.6 g (12.8 g/plant), as it can be observed in FIG. 7.

Figure 8:
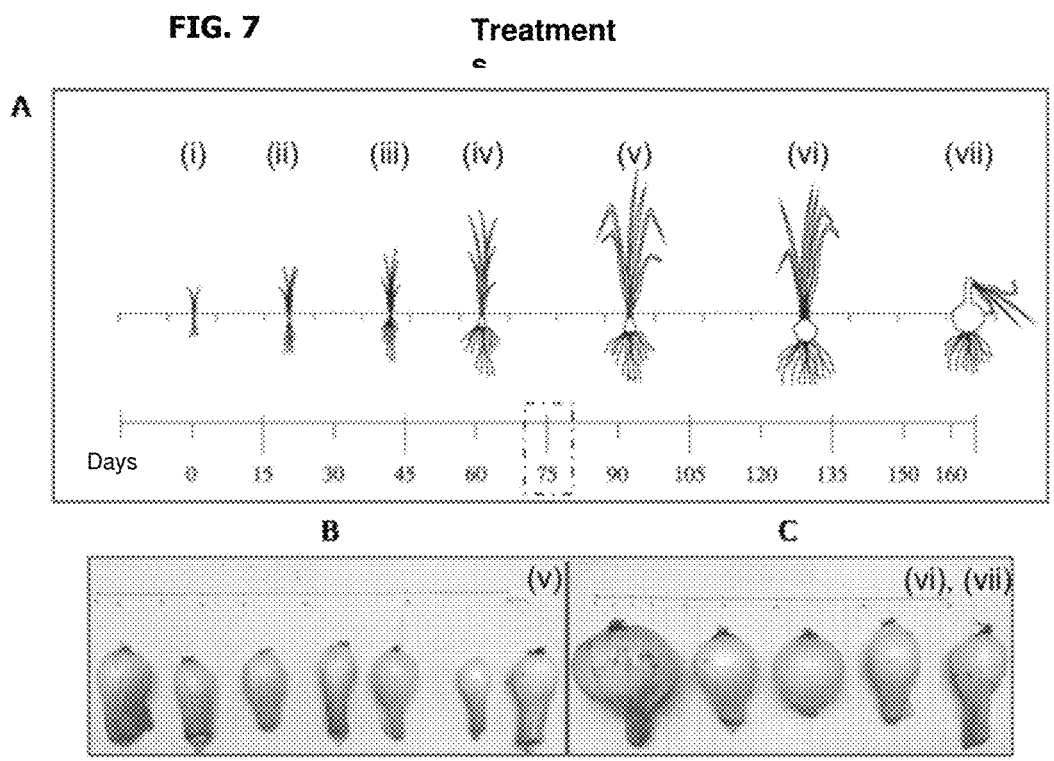
FIG. 8 shows the results from evaluating the yield of the biofertilizer (of the present invention) on spring onion cultivation. (A) physiological stages of onion development: (i) fourth leaf, (ii) leaf formation after transplant, (iii) apparition of 6th and 7th leaves, (iv) beginning of bulb formation, (v) thickening of bulb, (vi) mature bulb and (vii) fallen or dead leaves. (B) shows onions in control group within the bulb thickening stage (v), while in (C) onion bulbs cultured with the addition of the biofertilizers (BF) already show to be within the (vi) y (vii) physiological stages, i.e., mature bulb and fallen leaves stages.

As it can be observed after comparing FIGS. 8B and 8C with 8A, plants from control spring onion cultivation showed a physiological stage (v) corresponding to the onset of bulb formation. Meanwhile, spring onions treated with the biofertilizer showed later physiological stages, i.e., stages (vi) and (vii) corresponding to a well-formed mature bulbs. In other words, the biofertilizer of the present invention promoted a more effective plant growth, so the harvest time was reduced due to an acceleration to reach later plant physiological stages in less time. In other words, maturity was reached at 75 days, approximately 90 days earlier than the normal (165 days) cycle.

Example 9

Figure 9:
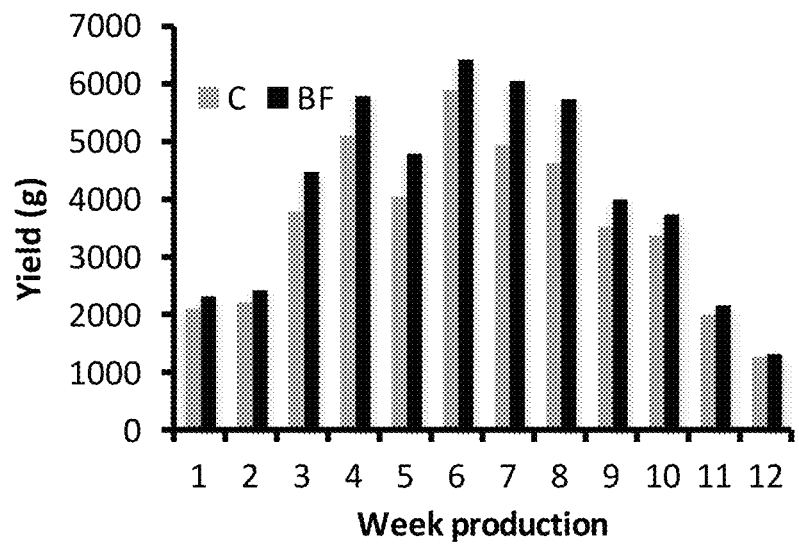
In FIG. 9, yield of the biofertilizer of the present invention on blueberry cultivation is shown.

To assess yield of the biofertilizer, 25 plants of a Blueberry var. Cielo were selected with a similar height from cultivation for massive commercial production during the beginning of the productive cycle. After trimming and one month of nutrition, biofertilizer was applied a single initial dose of 5 mL/plant with a cell density of $2.2 \times 10^{13}$ CFU/mL in plant stems at soil level. Biofertilizer was applied again at 30 and 60 days afterwards with a similar volume, but with a cell density of $2.4 \times 10^{13}$ and $2.1 \times 10^{13}$ CFU/mL respectively. All plants received normal nutrition by irrigation. Yield was quantitated by weighting fruits of each plant. Accumulated plant yield is shown in FIG. 9. Accumulated weight yield of plants treated with the biofertilizer was higher (49.195 kg or 1.97 kg/plant) than control (C) plants (42.969 kg or 1.72 kg/plant).

Example 10

To assess yield of the biofertilizer, three doses (cell density $2.1 \times 10^{13}$ CFU/mL) of it were applied to bell pepper plants every 15 days of cultivation in irrigation water at a proportion of 0.5 L of biofertilizer/150 L of irrigation water for 0.5 hectares in commercial protected agriculture conditions four months old (from the beginning of the productive cycle). 25 plants were selected for fruit weight monitoring in three intervals of one month each. Same procedure was applied for control plants. In table 2, results are shown. A 12.5 to 13.4% increase in yield was obtained with biofertilizer, as compared to control groups. Additionally, biofertilizer application increased the fruit size.

TABLE 2

| | Bell pepper fruit weight (Var. Canon) | | | | Increase | |
| --- | --- | --- | --- | --- | --- | --- |
| | with BF | | Control (no BF) | | respect to | |
| Cut | 1 fruit (g) | 5 fruits (kg) | 1 fruit (g) | 5 fruits (kg) | control (%) | Observations |
| 1 | 270 | 1.35 | 238 | 1.19 | 13.4 | Larger size with BF |
| 2 | 1 fruit (g) | 12 fruits (kg) | 1 fruit (g) | 12 fruits (kg) | 12.5 | Larger size with BF |
| | 270 | 3.24 | 240 | 2.88 | | |
| 3 | 260 | 3.12 | 230 | 2.8 | 13 | Larger size with BF |

Example 11

Figure 10:
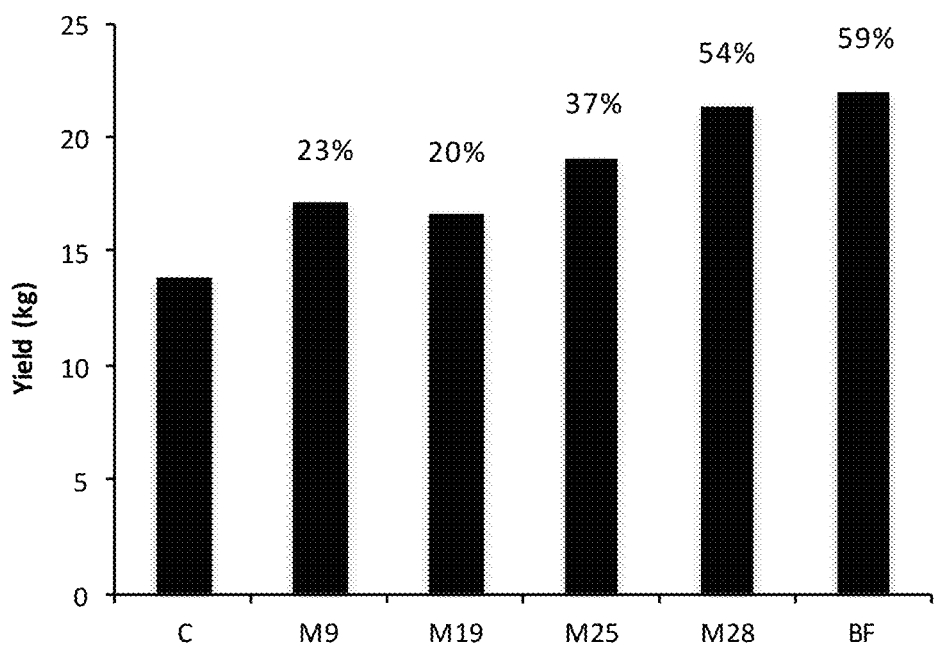
In FIG. 10, the plot shows the increase in cucumber cultivation yield by different microorganisms mixtures of the present biofertilizer.

To assess the synergic effect of the biofertilizer mixtures, the biofertilizer effect was compared with mixtures contained in it and with a control group. Bacterial mixtures were, as described in example 1: M9 (consisting of *Pseudomonas stutzeri, Pseudomonas denitrificans* and *Pseudomonas resinovorans*), M19 (consisting of *Pseudomonas brassicacearum* and *Pseudomonas fluorescens*), M25 (consisting of *Pseudomonas brassicacearum* and *Shimwellia blattae*) and M28 (consisting of *Klebsiella oxytoca* and *Shimwellia blattae*). 15 Cucumber plants with 30 days after transplantation were selected, nurtured in the normal way by using an irrigation water system. Biofertilizer or mixtures were applied in a single dose of 5 mL/plant on stem at soil level. Cell densities were: M9=$3.2 \times 10^{11}$ CFU/mL; M19=$5.2 \times 10^{11}$ CFU/mL; M25=$8.8 \times 10^{11}$ CFU/mL; M28=$1.6 \times 10^{11}$ CFU/mL, and whole biofertilizers BF $1.6 \times 10^{13}$ CFU/mL. Results are shown in FIG. 10. Mixtures increased production yield in 20-54% more than control yield, while biofertilizer increased yield in 59%. This result demonstrates the synergistic effect of the plant growth promoting bacteria conforming the consortium of the present invention for the enhancement of the agricultural yield.

Example 12

Figure 11:
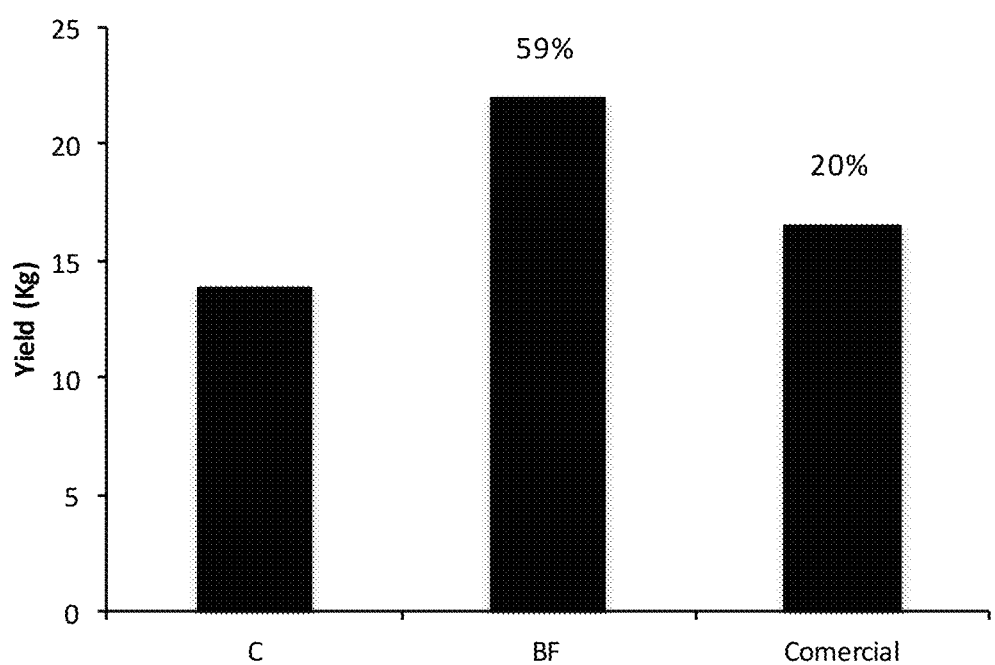
FIG. 11 shows the yield of the present biofertilizer (BF) compared to control treatment (no biofertilizer added, C), and to a commercially available biofertilizers.

To assess the yield of the consortium biofertilizer of the present invention was compared against a control and a commercial biofertilizer (HYTaEfficiency, MicrobialLife/Maya 2001) from the enterprise Agrinos S. A. de C. V. México, which contains microencapsulated cells of beneficial organisms (see below) and immobilized enzymes suspended in a biopolymer. According to its technical information sheet, this commercial biofertilizer: *Azotobacter vinelandii pasteurianum* ($3 \times 10^5$ CFU/mL), *Clostridium pasteurianum* ($3 \times 10^5$ CFU/mL), *Nitrosomonas, Nitrobacter, Pseudomonas, P. fluorescens, Microccocus, Lactobacter, Termoacetomicetos, Aspergillus, Lactobacillus, Bacillus subtilis, Bacillus Cereus, Bacillus thuringiensis, Bacillus megaterium, Rhizobian*, Cytokinine extracted from marine algae, Liche, *Trichoderma harzlanum* and *Thrichoderma viride*. 15 cucumber plants with 30 days from transplant, at the beginning of the production cycle were selected and nurtured and watered normally. A single 5 mL/plant dose was applied on stems at soil level with the following cell densities: biofertilizer of the present invention $1.6 \times 10^{13}$ CFU/mL, commercial biofertilizer $6 \times 10^5$ CFU/mL. Yield was assessed regarding the fruit weight of each plant during a month. Accumulated average fruit yield is shown in FIG. 11. Biofertilizer of the present invention increased fruit production yield in 50% respect to control, while commercial biofertilizer increased the fruit production yield in 20% respect to control C.

In accordance to that previously described, biofertilizer of the present invention has been developed to increase yield of diverse crops cultivation by means of the application of the biofertilizer, which also preserves a high cell density and therefore, has a longer shelf life. Moreover, for any expert in the area, it is evident that the different modes to increase agricultural yield, as previously described are only illustrative, i.e., they do not limit the application of the present invention, since there may exist a large amount of possible changes in the application, without affecting the scope of the present invention. For instance, different methods could be used to isolate or apply the bacteria, cell protectant or the vehicles suitable for agricultural use.

Therefore, the present invention should not be considered as restricted but only for the technique described above and the scope of the claims.

The invention claimed is:

1. A plant-growth formulation comprising:
a) an aqueous solution selected from the group consisting of dehydrated milk whey, potassium chloride, ammonium sulfate, iron sulfate, magnesium sulfate, manganese sulfate, and mixtures thereof; and
b) a culture of bacterial mixtures that comprises:
a first mixture comprising *Pseudomonas stutzeri, Pseudomonas denitrificans* and *Pseudomonas resinovorans;*
a second mixture comprising *Pseudomonas brassicacearum* and *Pseudomonas fluorescens;*
a third mixture comprising *Pseudomonas brassicacearum* and *Shimwellia blattae;* and
a fourth mixture comprising *Klebsiella oxytoca* and *Shimwellia blattae,*
wherein the culture of bacterial mixtures are isolated from a fermentation on an organic substrate, and wherein the organic substrate is selected from the group consisting of earthworm humus, milk whey, molasses, cow manure and mixtures thereof.

2. A biofertilizer comprising a plant-growth formulation comprising:
a) an aqueous solution selected from the group consisting of dehydrated milk whey, potassium chloride, ammonium sulfate, iron sulfate, magnesium sulfate, manganese sulfate, and mixtures thereof; and
b) a culture of bacterial mixtures that comprises:
a first mixture comprising *Pseudomonas stutzeri, Pseudomonas denitrificans* and *Pseudomonas resinovorans;*
a second mixture comprising *Pseudomonas brassicacearum* and *Pseudomonas fluorescens;*
a third mixture comprising *Pseudomonas brassicacearum* and *Shimwellia blattae;* and
a fourth mixture comprising *Klebsiella oxytoca* and *Shimwellia blattae,*
wherein the culture of bacterial mixtures are isolated from a fermentation on an organic substrate, and wherein the organic substrate is selected from the group consisting of earthworm humus, milk whey, molasses, cow manure and mixtures thereof.

3. The biofertilizer in accordance with claim 2, further including a plant-growth microorganism selected from the group consisting of a fungi, a rhizobacteria, and a native or mutant algae.

4. The biofertilizer in accordance to claim 3, wherein the bacterial mixture include in a one liter aqueous solution:
15-60 mL of the first mixture;
5-30 mL of the second mixture;
10-60 mL of the third mixture, and
5-30 mL of the fourth mixture.

5. The biofertilizer in accordance to claim 4, wherein the cell density of each mixture is:
in the $1 \times 10^9$ to $1 \times 10^{12}$ CFU/mL range;
in the $1 \times 10^9$ to $1 \times 10^{15}$ CFU/mL range; or
in the $1 \times 10^9$ and $1 \times 10^{13}$ CFU/mL range.

6. The biofertilizer in accordance to claim 2, wherein the dehydrated milk whey is in a concentration of 3-15 g/L of the aqueous solution.

7. The biofertilizer in accordance to claim 2, wherein the potassium chloride is in a concentration of 0.1-0.4 g/L of the aqueous solution.

8. The biofertilizer in accordance to claim 2, wherein the ammonium sulfate is in a concentration of 0.2-1.0 g/L of the aqueous solution.

9. The biofertilizer in accordance to claim 2, wherein the iron sulfate is in a concentration of 0.001-0.005 g/L of the aqueous solution.

10. The biofertilizer in accordance to claim 2, wherein the magnesium sulfate is in a concentration of 0.2 to 0.8 g/L of the aqueous solution.

11. The biofertilizer in accordance to claim 2, wherein the manganese sulfate is in a concentration of 0.002-0.009 g/L of the aqueous solution.

12. The biofertilizer in accordance to claim 2, further including a cell protectant.

13. The biofertilizer in accordance to claim 12, wherein the cell protectant is selected from a group consisting of: sodium alginate, gum arabic, polyvinylpyrrolidone, polyethylenglycol, trehalose, glycerol, high density carboxymethycelulose, polysorbate 20, and combinations thereof.

14. The biofertilizer in accordance to claim 12, wherein the cell protectant is added at a concentration of 0.1 to 2.5% w/v of the aqueous solution.

\* \* \* \* \*

SEQUENCE LISTING

<160> NUMBER OF SEQ ID NOS: 2

<210> SEQ ID NO 1
<211> LENGTH: 57
<212> TYPE: DNA
<213> ORGANISM: Artificial Sequence
<220> FEATURE:
<223> OTHER INFORMATION: Primer

<400> SEQUENCE: 1
cgcccgccgc gccccgcgcc cgtcccgccg ccccccgcccc cctacgggag gcagcag      57

<210> SEQ ID NO 2
<211> LENGTH: 17
<212> TYPE: DNA
<213> ORGANISM: Artificial Sequence
<220> FEATURE:
<223> OTHER INFORMATION: Primer

<400> SEQUENCE: 2
attaccgcgg ctgctgg      17